United States Patent [19]

Schatz

[11] Patent Number: 5,362,446
[45] Date of Patent: Nov. 8, 1994

[54] CONTAINMENT OF AN AEROSOLABLE LIQUID JET

[75] Inventor: Klaus W. Schatz, Lawrenceville, N.J.

[73] Assignee: Mobil Oil Corporation, Fairfax, Va.

[21] Appl. No.: 133,402

[22] Filed: Oct. 8, 1993

Related U.S. Application Data

[63] Continuation-in-part of Ser. No. 950,354, Sep. 24, 1992, Pat. No. 5,286,456.

[51] Int. Cl.$^5$ .............................................. G05B 9/00
[52] U.S. Cl. ................................... 422/117; 422/105; 585/723; 585/724; 585/725; 285/13
[58] Field of Search ............................. 422/105, 117; 585/723–725; 137/177, 171, 154; 239/121–122, 343; 137/312–314; 285/13

[56] References Cited

U.S. PATENT DOCUMENTS

| | | | |
|---|---|---|---|
| 388,260 | 8/1888 | Carey | 285/13 |
| 425,369 | 4/1890 | Cowell | 285/13 |
| 1,438,199 | 12/1922 | Voges | 239/343 |
| 2,699,960 | 1/1955 | Callery et al. | 285/13 |
| 2,796,297 | 6/1957 | Klock | 239/343 |
| 3,716,343 | 2/1973 | Chapman | 422/215 |
| 3,795,712 | 3/1974 | Torck et al. | 585/455 |
| 4,210,460 | 7/1980 | Seidenberger | 134/7 |
| 4,273,285 | 6/1981 | Scholbrock | 239/121 |
| 4,472,268 | 9/1984 | Olah | 208/134 |
| 4,552,624 | 11/1985 | Clarkson | 204/153.13 |
| 4,938,935 | 7/1990 | Audeh et al. | 423/240 R |
| 4,938,936 | 7/1990 | Yan | 423/240 R |
| 4,939,833 | 7/1990 | Thomas | 137/312 |
| 5,041,146 | 8/1991 | Simmerlein-Erlbacher | 55/233 |
| 5,073,674 | 12/1991 | Olah | 585/725 |
| 5,098,668 | 3/1992 | Callen et al. | 422/111 |
| 5,277,881 | 1/1994 | Partridge, Jr. et al. | 422/241 |

OTHER PUBLICATIONS

Hazardous Material Spills Conference Proceedings, 1982, F. C. Norman, pp. 363–365.
Kirk-Othmer Encyclopedia of Chemical Technology, 3rd Ed. vol. 1, pp. 624–655.
Gordon K. Braley, Several Remedies for the Treatment of Spillages of Liquid Hazardous Chemicals, pp. 103–108.
Mitigation of Aerosol Releases, Hans K. Fauske, Presentation to HF User Group, Amoco Corp., Chicago, Ill., Mar. 25, 1988, 13 pp.
Aerosol Reduction from Episodic Releases of Anhydrous HF Acid by Modifying the Acid Catalyst with Liquid Opium, Comey et al., Presentation to AIChE 1993 Summer National Meeting, Aug. 16, 1993, pp. 1–17.

*Primary Examiner*—Robert J. Warden
*Assistant Examiner*—Hien Tran
*Attorney, Agent, or Firm*—A. J. McKillop; M. D. Keen

[57] ABSTRACT

A method of increasing rainout from a liquid jet of an aerosolable corrosive and toxic substance, e.g. hydrogen fluoride, hydrofluoric acid, ammonia or chlorine, exiting from a pressurized source, such as a vessel, conduit, pump. The method includes spacing an impact plate from the pressurized source for deflecting the liquid jet to dissipate forward velocity and energy of the liquid jet. The impact plate is positioned a distance from the pressurized source to impact the liquid jet before the liquid is capable of expanding to form a substantial aerosol of vaporized substance. A mesh pad abuts the impact plate and faces the pressurized source for initially reducing the velocity and energy of the liquid jet, and for preventing back and radial splash of the liquid jet deflecting off the impact plate to coalesce droplets of the substance and thereby produce a collectable run-off.

26 Claims, 2 Drawing Sheets

CONTAINMENT OF AN AEROSOLABLE LIQUID JET

CROSS-REFERENCE TO RELATED APPLICATION

This application is a continuation-in-part of U.S. Patent application Ser. No. 07/950,354, filed Sep. 24, 1992 now U.S. Pat. No. 5,286,456.

BACKGROUND OF THE INVENTION

1. Field of the Invention

The present invention relates to a method for containing and neutralizing a liquid jet of an aerosolable corrosive and toxic substance such as hydrogen fluoride (HF), hydrofluoric acid, ammonia, chlorine and the like. More particularly, the present invention relates to a method for increasing rainout from a liquid jet of such substance and thereby minimize aerosol formation.

2. Description of Prior Art

Hydrofluoric acid is toxic and corrosive. In gaseous vapor or liquid form, hydrofluoric acid attacks the skin, and will on contact cause ulceration of mucous membranes and possibly chemical pneumonia to those exposed to it. Hydrofluoric acid is, however, an industrially important chemical. It is used to manufacture fluorine and to prepare fluorides and other chemical compounds. It is also used as a catalyst for isomerization, condensation, polymerization and hydrolysis reactions. The petroleum industry uses anhydrous hydrogen fluoride primarily as a liquid catalyst for the alkylation of olefinic hydrocarbons to produce alkylate for increasing the octane number of gasoline.

The petroleum refining industry has always recognized the potential for hazard created by HF alkylation units. Accordingly, the industry has consistently ensured that a high level of safety is maintained by use of superior mechanical and metallurgical specifications, and operational practices in the design, construction and operation of these units. As a result, the HF alkylation process has enjoyed an almost unparalleled record of industrial safety. However, the industry has continued to seek enhancement of the intrinsic safety of these units to secure a higher level of potential operating safety and to guard against the consequences of an uncontrolled release of unit contents.

The potential magnitude of the risk inherent in operating an HF alkylation unit may be reduced by a number of qualitative methods that have been proposed for treating HF spills. The most common method is the use of a simple water drench system. Kirk-Othmer Encyclopedia of Chemical Technology, 3rd Edition, Volume 1, page 655 reports that water the most common absorption liquid is used for removing acidic gases, especially if the last contact is with water of alkaline pH. However, because of the aerosol nature of an HF cloud in which the HF droplets are in the order of 0.1 micron and thus very small compared to droplets of water in a simple water drench, the water drench generally has difficulty in removing all the HF present in the cloud.

U.S. Pat. No. 4,210,460 relates to treating an HF liquid spill by applying to the spill a quantity of an aqueous solution of calcium acetate equal to at least seven times the estimated volume of the spill, and thereafter treating the spill with powdered magnesium oxide. The mixture is tested using a pH indicator such as bromothymol blue. After the mixture reaches a persistent blue color, indicating a safe state, the spill is cleaned up mechanically.

At the 1982 Hazardous Material Spills Conference, Edward C. Norman of National Foam System Inc reported the application of limestone and then CHF-784 foam (a proprietary composition) to the contents of a damaged tank emitting an HF cloud. An immediate reduction in fume evolution was apparent after the foam application.

Gordon K. Braley, at the proceedings of the 1980 National Conference on Control of Hazardous Material Spills, in Louisville, Kentucky on May 15, 1980 reported the treatment of relatively small amounts of controlled liquid spills of anhydrous hydrogen fluoride with high molecular weight polymers including polyacrylamide, polymethyl methacrylate, and polyvinyl alcohol. These materials applied in the form of a bead polymer formed a skin over the spill preventing fuming of the liquid. Polyacrylamide was deemed the most effective skin-forming agent.

SUMMARY OF THE INVENTION

The present invention was devised to provide an effective method for containing and neutralizing a liquid jet before it can form a corrosive and toxic cloud. In accordance with the present invention there is provided a method of increasing rainout from a liquid jet of an aerosolable corrosive and toxic substance, e.g. hydrogen fluoride, hydrofluoric acid, ammonia or chlorine, exiting from a pressurized source such as a vessel including a reactor, a conduit, a pump or the like. The method includes spacing an impact plate from the source for deflecting the liquid jet to dissipate forward velocity and energy of the liquid jet. A mesh pad is positioned in abutting engagement with the impact plate and facing the source for initially reducing the velocity and energy of the liquid jet, and for preventing back and radial splash of the liquid jet deflecting off the impact plate to coalesce droplets of the substance and thereby produce a collectable run-off. The mesh pad preferably has a thickness of from about 0.5 inches to about 10 inches, and a mesh of from about 0.01 inch to about 0.25 inch.

The impact plate is preferably normal to the direction of the liquid jet, and must be constructed with a suitable thickness and material to withstand the force of the liquid jet. As soon as the liquid jet leaves the pressurized source, it is under atmospheric pressure and its pressure is converted into liquid velocity. The liquid then has a momentum which exerts a force on the impact plate in accordance with the following formula.

$$F = \rho q V / g_c \qquad \text{Eq.1}$$

wherein

F = force acting on the impact plate, lb. force;
$\rho$ = fluid density, lb/cu. ft.;
q = volumetric flow rate,cu.ft./sec.;
V = velocity, ft./sec.; and
$g_c$ = dimensional constant, 32.17 (lb.) (ft.)/(lb. force) (sec$^2$).

The material for the impact plate should be corrosion resistant such as carbon steel plate, or acid resistant plastic such as polypropylene or PVC, and have a thickness and possibly a support backing sufficient to withstand the force (F).

The impact plate and mesh pad are positioned a distance from the source to impact the liquid jet before the liquid jet is capable of expanding to form a substantial aerosol of vaporized substance. This distance is may be from about 0.5 inch to about 50 feet, and preferably from about 3 inches to about 10 feet, depending upon pressure, temperature and composition of the substance. As the pressure increases, the preferred distance may also increase (or the thickness of the pad may be increased). Expressed another way the impact plate and mesh pad limit the atmospheric residence time (time of flight) of the liquid jet from about 5 milliseconds to about 500 milliseconds. The time of flight is equal to the distance between the pressurized source and the impact plate divided by the velocity of the liquid jet, where the velocity is determined by the following formula.

$$V_o = C[2g_c(p_2 - p_1)/\rho_0]^{\frac{1}{2}} \qquad \text{Eq.2}$$

wherein
$V_o$ = velocity of liquid jet(ft./sec.);
c = coefficient,dimensionless;
$g_c$ = dimensional constant, 32.17 (lb.)(ft.)/(lb.force)(sec$^2$);
$P_1$ = pressure outside the source(lb.force/sq.ft.);
$P_2$ = pressure inside the source(lb.force/sq.ft.);and
$\rho_0$ = liquid density(lb/cu.ft.).

Eq.1 and Eq.2 are described in detail in Perry's Chemical Engineers' Handbook, 5th Ed., McGraw-Hill Book Company at pages; 5-19 and 5-8, respectively, which pages are incorporated herein by reference.

DESCRIPTION OF SPECIFIC EMBODIMENTS

Figure 1:
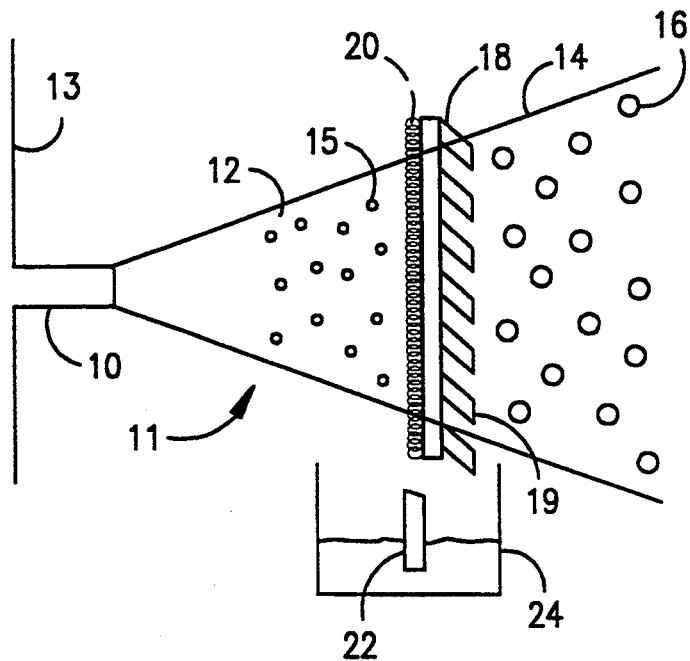
FIG. 1 is a schematic view of an expanding liquid jet with aspects of an embodiment of the present invention.

With reference to FIG. 1, there is diagrammatically shown a liquid HF jet 10 exiting a source such as a vessel 13 and expanding at 12 by entraining air 15 to rapidly form an aerosol 14 from vaporized HF 16. Typically, the corrosive and toxic substance is above its boiling point and thus enhances the potential for forming an aerosol in the event of a leak. For example, hydrogen fluoride, ammonia and chlorine boil at 19.4° C. −33.4° C. and −34.6° C., respectively.

In accordance with the present invention, when an impact plate 18 with support hacking 19 and a mesh pad 20 are placed in the expanding cone 11, the impact plate deflects the liquid jet 10. The mesh pad 20 abuts the impact plate 18 and faces the source 13 for initially reducing the velocity of the liquid jet 10 and for preventing hack and radial splash of the liquid jet deflecting off the impact plate 18 to thereby coalesce droplets of the HF and produce a collectable rainout or run-off 22 which is collected in a basin 24 beneath the pad 20. The pad 20 preferably has a thickness of from about 0.5 inch to about 10 inches, and a mesh of from about 0.01 inch to about 0.25 inch.

The impact plate 18 and mesh pad 20 are positioned a distance from the source 13 to impact the liquid jet 10 before the liquid jet is capable of expanding to form a substantial aerosol of vaporized HF. The distance may be from about 0.5 inch to about 50 feet, and preferably from about 3 inches to about 10 feet. The impact plate 18 may suitably be ⅛ inch PVC with a reinforced frame as a backing 19.

HF and HF/Additive tests were performed to evaluate the aerosol forming tendencies of different HF/Additive mixtures. For this purpose a flow chamber was designed having a target plate with a pad of fine steel wool installed in the flow chamber to prevent any fine drops of liquid from splashing sideways and getting entrained into the outlet of the chamber. Liquid drops impacting on the pad quickly coalesced and formed a more or less continuous rivulet of liquid dropping into the collection compartments below much as shown in FIG. 1. It was found that aerosol formation was reduced and rainout was increased for anhydrous HF with a shorter distance between the source outlet and target plate.

Large scale field tests of HF/Additive were conducted in a longer flow chamber. The flow chamber was long enough to allow full trajectories for the liquid released from an orifice at the front end of the chamber. As shown in Tests 34 and 33 of the following Table, the increased time of flight substantially decreased rainout and increased aerosol formation. However, as shown by Tests 36 and 37 of the Table, installation of an impact plate covered with steel mesh demistor pads at approximately 3 feet from the orifice increased rainout by about 35–40%.

TABLE

| | HF/Additive Tests | | | | |
|---|---|---|---|---|---|
| Test No | HF concentration wt % | Pressure psig | Temperature °F. | Impact Plate & Pad Yes/No | Rainout wt % |
| 34 | 50 | 140 | 110 | N | 64 |
| 36 | 50 | 140 | 110 | Y | 99 |
| 33 | 66 | 140 | 90 | N | 53 |
| 37 | 69 | 140 | 90 | Y | 94 |

Based on these test data the advantages of truncation of liquid jets of HF and HF/Additives in accordance with the present invention is evident. Applying the concept to an alkylation unit or any liquid container of high HF concentration requires some adaptation to the site specific design details of the equipment that might produce an accidental HF leak.

Figure 2:
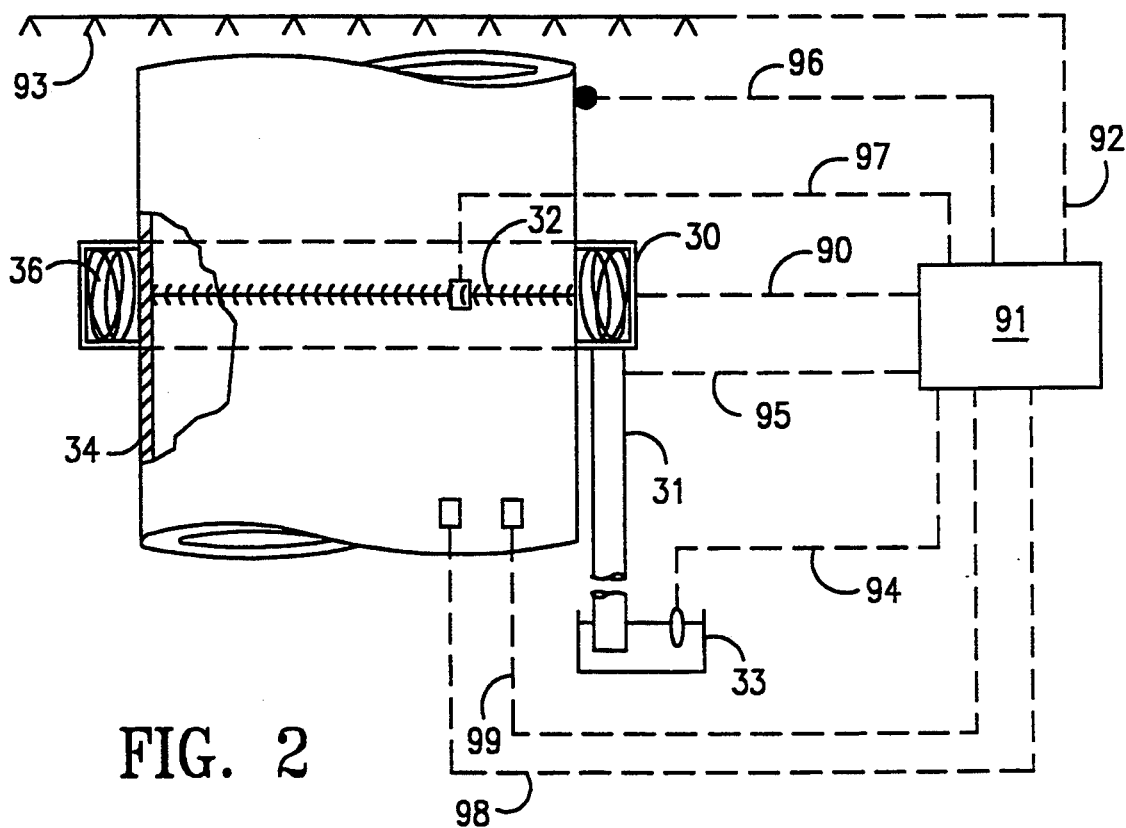
FIG. 2 is a diagrammatic side view of a vessel or conduit having an aspect of the present invention covering a circumferential weld.

In FIG. 2, the impact plate is a U-shaped annulus 30 positioned about a weld seam 32 of a vessel or pipe 34. A conduit or drain pipe 31 feeds the run-off from the annulus plate 30 to a basin 33.

As in all the embodiments disclosed herein, the pad 36 positioned within the annulus 30 can consist of nonreactive material like stainless steel wool, plastic fiber or matting. In another approach the pad can consist of reacting material like glass wool, stone wool, plastic fiber matting impregnated with metal oxides like $TiO_2$, metal carbonates like $NaHCO_3$, metal hydroxides like $Ca(OH)_2$, or with metal powders like aluminum. Aluminum shavings would also be applicable as a reacting type padding. The reacting materials would neutralize the HF. The pad may also be impregnated with materials to modify physical properties of HF, such as a surfactant to improve rainout.

FIG. 2 also provides a system where any major leak would exert a mechanical force on the inside of the impact plate 30. This force could be used to create a mechanical (lever/relay), or an electrical (load-cell) signal 90 to a computer 91 which in turn sends a signal 92 to trigger water sprays 93 to enhance the mitigation of an HF leak. Similarly, triggering based on a change of pH signal 94 in the collecting basin 33 or based on a flow detection signal 95 from the drain pipe 31 could be used. This spray system may be used in any of the embodiments of the invention.

In one aspect of the present invention, HF detectors 96, 97 are placed about the top periphery of the vessel 34 (storage tank or tower) containing HF alkylation acid and about at mid-portion of such a storage facility, respectively. The detectors 96,97 should also be located at weld seams, pipe connections and other conduits used for transporting HF alkylation acid to the alkylating reactor, where a leak might occur.

A suitable primary HF detector is disclosed U.S. Pat. No. 4,552,624 which is incorporated herein by reference. Primary HF detectors can monitor an initial HF leak and transmit such information to a computer 91 which then activates the drenching steps discussed above.

Additional electro-mechanical devices such as secondary detectors can also be used in combination with the HF detectors to determine and verify the extent of the leak. For instance, the temperature of the walls of an HF containment vessel or alkylating unit, and the pressure within the tank and feed lines can be constantly monitored. As shown in FIG. 2, the computer 91 oversees the collection of data registered by the devices, including the primary HF detectors 96,97 and the secondary temperature or pressure detectors 98,99. When the collected data indicates a leak, such as by a predetermined pressure change and temperature change, which are associated with such a leak, the computer 91 activates the spray system.

Figure 3:
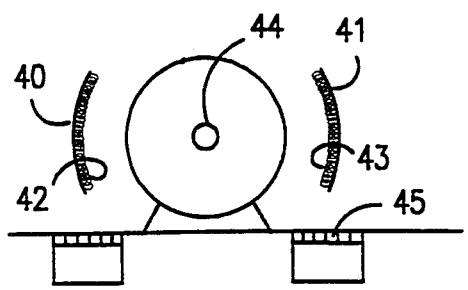
FIG. 3 is a diagrammatic view of a pump with another embodiment of the present invention.

With reference to FIG. 3, the impact plates 40,41 and pads 42,43 are arcuately shaped about a pump seal 44 to contour the periphery of the seal 44. These impact plates 40,41 are particularly useful for small areas of relatively high failure frequency such as pump seals. For easy access, the plates 40,41 are preferably placed up to 3 feet from the potential leak source or may be made removable. Run-off from the pads 42,43 is collected in a trench 45 connected to an acid sewer (not shown). The trench 45 can be filled with water, or with $CaCl_2$, caustic, calcium carbonate such as crushed limestone or crushed sea shells, or any of the other reacting materials listed above to dilute or neutralize the run-off. If the trench 45 is open to rain, then calcium carbonate is preferred over $CaCl_2$ or caustic because it is resistant to rain water. Water is used in the trench 45 to suppress HF fuming by diluting the run-off. A particularly useful combination is locating water and calcium carbonate in the trench to provide a double effect of the water suppressing HF fumes from the run-off by dilution and of the calcium carbonate neutralizing the run-off.

Figure 4:
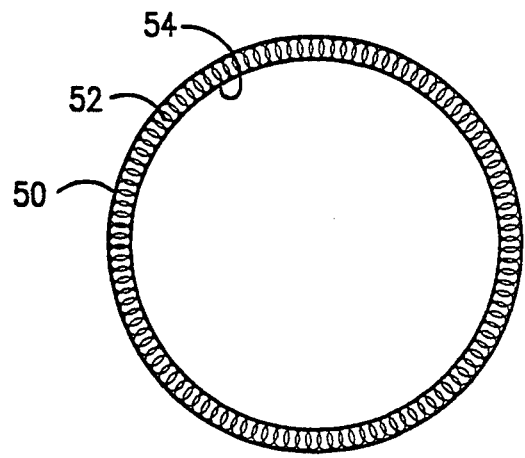
FIG. 4 is a top view of a vessel or conduit encased with still another embodiment of the invention.

With reference to FIG. 4, an impact plate 50 and pad 52 encase at least a substantial portion of a vessel or conduit 54 with the pad additionally functioning as an insulator. In this instance the plate 50 should be made of acid resistant material, and preferably be spaced at least about 3 inches from the vessel or conduit 54. In an HF alkylation system, suitable areas for encasement are the reactor, the acid settler, settler boot, piping or conduits especially at welds, and the product recovery unit.

Figure 5:
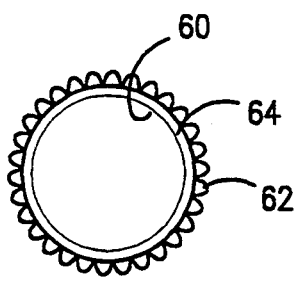
FIG. 5 is a top view of another vessel or conduit with a corrugated embodiment of the invention.

As shown in FIG. 5, vertical pipes and vessels 60 can have an impact plate 62 that is corrugated and fitted about the cylindrical pipe or vessel 60 forming an annular space therebetween. The mesh pad 64 is located in the annular space. The corrugated plate 62 provides faster draining of the liquid, and may be transparent plastic to better identify a leak location.

Figure 6:
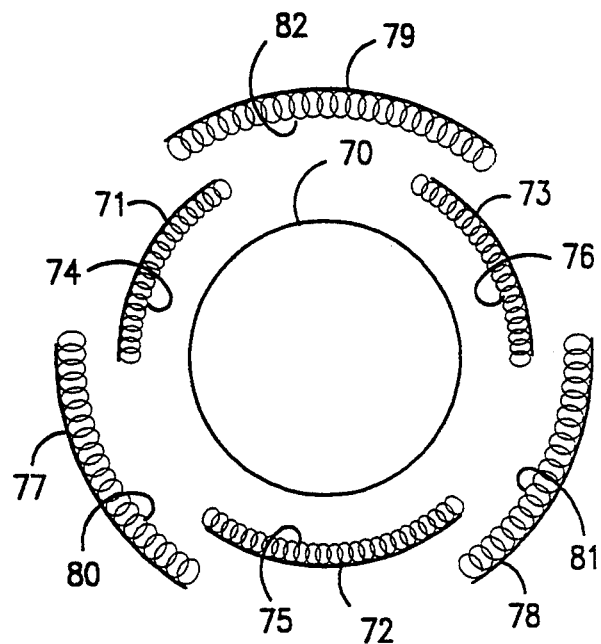
FIG. 6 is a top view of a vessel or conduit circumscribed by yet another embodiment of the invention.

FIG. 6 shows another embodiment wherein an HF containing vessel or conduit 70 has a first plurality of impact plates 71,72,73 and pads 74,75,76 arcuately shaped and spaced apart at a first radial distance from the vessel or conduit 70. A second plurality of impact plates 77,78,79 and pads 80,81,82 are arcuately shaped and spaced apart at a second radial distance from the vessel or conduit 70. The second plurality of impact plates and pads fill the spaces between said first plurality of impact plates and pads to thereby circumscribe the vessel or conduit 70 with the impact plates and pads while personnel have access between the plates and pads to the vessel or conduit 70. This embodiment permits ready dispersion of hydrocarbons while containing and neutralizing the HF component of a leak.

Two types of HF alkylation units are in general use at the present time. In the gravity flow type reactor, the hydrocarbon reactants meet the liquid by hydrofluoric acid entering the bottom of the reactor from an acid cooler to which the acid flows from an acid settler after the alkylation reaction has taken place. The driving force for the circulation of the acid and the hydrocarbon reactants is the difference in density between the catalyst and the hydrocarbons at different points in the system aided by the jet action of the injection nozzles in the reactor. The acid settler permits a phase separation to take place between the denser acid phase and the lighter hydrocarbon phase. The acid phase is recycled to the acid cooler and then back to the reactor; the hydrocarbon phase including the alkylation product is fed to a fractionation section where the propane and unreacted isobutane are separated from the motor fuel alkylate fraction. The isobutane is recycled and propane is removed from the unit. Units of this type are described in U.S. Pat. Nos. 3,716,343, and 5,098,668 which are incorporated herein by reference.

The other principal type of unit currently in use is the pumped acid flow type in which the mixed hydrocarbon feed is introduced into the reactor through spargers along the vertical length of the reactor. From the reactor the catalyst and the hydrocarbons flow into an acid settler where a phase separation takes place in the same way as in the gravity flow unit, permitting product and catalyst recovery in the same manner as described above. Compared to the gravity flow reactor, the pumped circulation reactor uses a smaller inventory of acid because of the higher circulation speed of the catalyst in this type of unit and the smaller size of the piping utilized in the unit. This type of unit is also described in U.S. Pat. No. 5,098,668 which is incorporated herein by reference.

An HF alkylation acid composition is typically composed of about 88% HF, 6.5% acid-soluble oils, 4% hydrocarbons, predominantly isobutane, and 1.5% water. However, HF may be used in combination with up to about 50% of various additives which may be present either to reduce the aerosol-forming tendency of HF, usually by reducing its vapor pressure, to improve the alkylation process or to modify the properties of the HF so that any accidental release may be more readily controlled. For example, the aerosol may be rendered more susceptible to water drench. The use of sulfolane for improving the alkylation characteristics of acid catalysts is described in U.S. Pat. No. 3,795,712. The use of various proton acceptors including various phosphorus compounds is described in U.S. Pat. No. 4,938,935. Alkylation catalysts including HF and other catalysts and additional components are described in U.S. Pat. No. 4,472,268 and East German Patent Nos. 271,322 and 243,923. U.S. Pat. Nos. 3,795,712 and 4,938,935, and East German Patents Nos. 271,322 and 243,923 are incorporated herein by reference.

A preferred HF catalyst composition for reducing the tendency of HF to form an aerosol cloud in the event of a leak or spill is from about 1.0 wt % to about 3.0 wt % water; from about 20 wt % to about 40% sulfolane, with the more preferred range of sulfolane being from about 25 wt % to about 35 wt %; and from about 57 wt % to about 79 wt % hydrofluoric acid.

Another HF catalyst composition suitable for reducing the tendency of HF to form an aerosol cloud includes a liquid onium polyhydrogen fluoride complex as the reaction medium. Some examples of polyhydrogen fluoride complexes include those of ammonia, methylamines, ethylamines, propylamines, butylamines, pyridine, picolines, pentylamines, melamines and hexamethylenetetramine. The concentration of the amine components of the hydrofluoric acid complex is between 5 and 30 wt %, and anhydrous hydrogen fluoride is present in an amount of between 70 to 95 wt %. This catalyst composition is disclosed in U.S. Pat. No. 5,073,674, which patent is hereby incorporated herein by reference.

The use of controlled amounts of sulfolane as an additive for HF to control the aerosol-forming tendencies of the acid is described in U.S. Patent applications Ser. No. 07/860,966, filed Mar. 31, 1992, now abandoned, and Ser. No. 07/856,270, filed Mar. 23, 1992. Reference is made to applications Ser. Nos. 07/856,270 and 07/860,966 for detailed descriptions of these processes using combinations of HF and sulfolane, alone or with water, and both of these applications are incorporated herein by reference.

As noted above, the present invention is also suitable for containment of aerosolable liquid jets of chlorine and ammonia. These substances have wide commercial uses such as chlorine in the chlorination of water, and ammonia in controlling NOx emissions in fluid catalytic cracking units. The various impact plate and pad embodiments of the invention also have utility in knocking down corrosive and toxic substances having a high boiling point, such as sulfuric acid used for alkylation.

While the invention has been described in conjunction with specific embodiments thereof, it is evident, that many alternatives, modifications, and variations will be apparent to those skilled in the art in light of the foregoing description. Accordingly, it is intended to embrace all such alternatives, modification, and variations as fall within the spirit and broad scope of the appended claims.

What is claimed is:

1. A method of increasing rainout from a liquid jet of an aerosolable corrosive and toxic substance exiting from a pressurized source comprising the steps of:

spacing an impervious impact plate from a pressurized source for deflecting the liquid jet of an aerosolable corrosive and toxic substance exiting from said pressurized source to dissipate forward velocity and energy of said liquid jet;

positioning a mesh pad in abutting engagement with said impact plate and facing said pressurized source for initially reducing the velocity of said liquid jet and for preventing back and radial splash of the liquid jet deflecting off said impervious impact plate to thereby coalesce droplets of said aerosolable corrosive and toxic substance and produce a run-off;

collecting said run-off; and neutralizing the collected run-off.

2. The method of claim 1 wherein said impact plate and said pad are positioned a distance from said source to impact said liquid jet before said liquid jet expands to form a substantial aerosol of vaporized substance.

3. The method of claim 2 wherein said aerosolable corrosive and toxic substance comprises hydrogen fluoride and up to 50% by weight of an additive for reducing the tendency of said hydrogen fluoride to form an aerosol.

4. The method of claim 3 wherein said additive is sulfolane.

5. The method of claim 4 wherein from about 20% to about 40% by weight of said sulfolane is added to said hydrogen fluoride.

6. The method of claim 2 wherein said aerosolable corrosive and toxic substance comprises an alkylation catalyst composition comprising hydrofluoric acid.

7. The method of claim 6 in which said catalyst composition comprises from about 1.0 wt. % to about 3.0 wt. % water, from about 20 wt. % to about 40 wt. % sulfolane and from about 57 wt. % to about 79 wt. % hydrofluoric acid.

8. The method of claim 7 wherein said catalyst composition includes from about 25 wt % to about 35 wt % sulfolane.

9. The method of claim 3 wherein said distance is from about 0.5 inch to about 50 feet.

10. The method of claim 3 wherein said distance is from about 3 inches to about 10 feet.

11. The method of claim 3 wherein said liquid jet is in flight to said impact plate and said pad for from about 5 milliseconds to about 500 milliseconds.

12. The method of claim 3 wherein said Dad has a thickness of from about 0.5 inch to about 10 inches, and a mesh size of from about 0.01 inch to about 0.25 inch.

13. The method of claim 3 wherein said impact plate is positioned normal to said liquid jet, and is formed of corrosion resistant material.

14. The method of claim 2 wherein said aerosolable substance is selected from the group consisting of hydrofluoric acid, hydrogen fluoride, ammonia and chlorine.

15. The method of claim 3 wherein said pad is formed of a non-reactant material.

16. The method of claim 15 wherein said non-reactant material is stainless steel wool or plastic fiber matting.

17. The method of claim 3 wherein said pad is formed of a reactive material.

18. The method of claim 17 wherein said reactive material is glass wool, stone wool or plastic fiber matting impregnated with metal oxide, metal carbonate, metal hydroxide or metal powder.

19. The method of claim 18 wherein said reactive material is impregnated with $TiO_2$, $NaHCO_3$, $Ca(OH)_2$ or aluminum powder.

20. The method of claim 3 wherein said run-off is collected in a trench leading to an acid sewer.

21. The method of claim 20 further comprising lining said trench with an agent for neutralizing said run-off.

22. The method of claim 21 wherein said agent is calcium carbonate.

23. The method of claim 22 wherein said calcium carbonate is in the form of crushed limestone or sea shells.

24. The method of claim 20 further comprising providing water in said trench for diluting said run-off and thereby suppressing hydrogen fluoride fumes.

25. The method of claim 24 further comprising lining said trench with calcium carbonate for neutralizing said run-off.

26. The method of claim 3 and further comprising generating a signal in response to a leak of said liquid jet, and activating a spray in response to said signal to water down said liquid jet.

* * * * *